US00PP20128P3

(12) United States Plant Patent
Goffreda et al.

(10) Patent No.: US PP20,128 P3
(45) Date of Patent: Jun. 30, 2009

(54) PEACH TREE NAMED 'NJF15'

(50) Latin Name: *Prunus persica*
Varietal Denomination: NJF15

(75) Inventors: Joseph C. Goffreda, Manalapan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 389 days.

(21) Appl. No.: 11/371,755

(22) Filed: Mar. 9, 2006

(65) Prior Publication Data

US 2007/0214525 P1 Sep. 13, 2007

(51) Int. Cl.
*A01H 5/00* (2006.01)

(52) U.S. Cl. ..... Plt./197

(58) Field of Classification Search ..... Plt./197
See application file for complete search history.

*Primary Examiner*—Annette H Para
*Assistant Examiner*—Georgia Helmer
(74) *Attorney, Agent, or Firm*—James A. Lucas; Driggs, Hogg, Daugherty & Del Zoppo Co., LPA

(57) ABSTRACT

A new and distinct peach variety of *Prunus persica* named 'NJF15' is provided. This variety is distinguished from other peach varieties by its unique combination of large, showy, light pink flowers, flat fruit that ripen in early midseason with mottled red over color on a bright yellow-orange ground color, clingstone fruit with a juicy, nonmelting texture and sweet, spicy flavor, firm fruit that retain their firmness well and trees with regular, heavy production of fruit.

6 Drawing Sheets

Latin name of genus and species of the plant claimed: *Prunus persica* L.
Cultivar name: NJF15.

BACKGROUND OF THE INVENTION

The present invention relates to a new and distinct variety of peach tree named 'NJF15'. Our new tree resulted from crossing 'B7-151-752080' (unpatented) as the seed parent with 'NJF7' peach tree (unpatented), as the pollen parent. The new variety differs from seed parent 'B7-6- 151-752080' (unpatented) in that the new variety has green leaves while the seed parent has red leaves. The new variety differs from pollen parent 'NJF7' in that the new variety has yellow flesh while the pollen parent has white flesh. The resulting tree was selected when growing in a cultivated area as the 270$^{th}$ tree in the 51$^{st}$ row of Block D at the Rutgers Fruit Research and Extension Center in Cream Ridge, N.J.

BRIEF SUMMARY OF THE INVENTION

The 'NJF15' variety is distinguished from other peach varieties due to the following unique combination of characteristics:

Flat fruit shape.

Fruit with mottled red over color on a bright yellow-orange ground color.

Sweet, spicy flavor.

Nonmelting flesh texture.

Very firm fruit that retain their firmness well.

The variety was asexually reproduced in Cream Ridge, N.J. Asexual reproduction of this new variety by budding onto >Lovell=rootstock (unpatented) for several generations shows that the foregoing characteristics are so reproduced.

The following detailed description concerns the original tree, 'NJF15'. The original tree and asexual progeny have been observed growing in a cultivated area in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

BRIEF DESCRIPTION OF THE DRAWINGS

This new variety is illustrated by the accompanying photographic drawings, depicting the peach tree by the best possible color representation using color photography. All color references below are measured against The Royal Horticultural Society (R.H.S.) Colour Chart. Colors are approximate as color depends on horticultural practices, such as light level, fertilization rate, and other conditions and, therefore, the color characteristics of this new variety should be determined with reference to the observations described herein, rather than from these illustrations alone. The following photographs were taken of a typical tree that was nine (9) years of age.

DETAILED BOTANICAL DESCRIPTION

Figure 1:
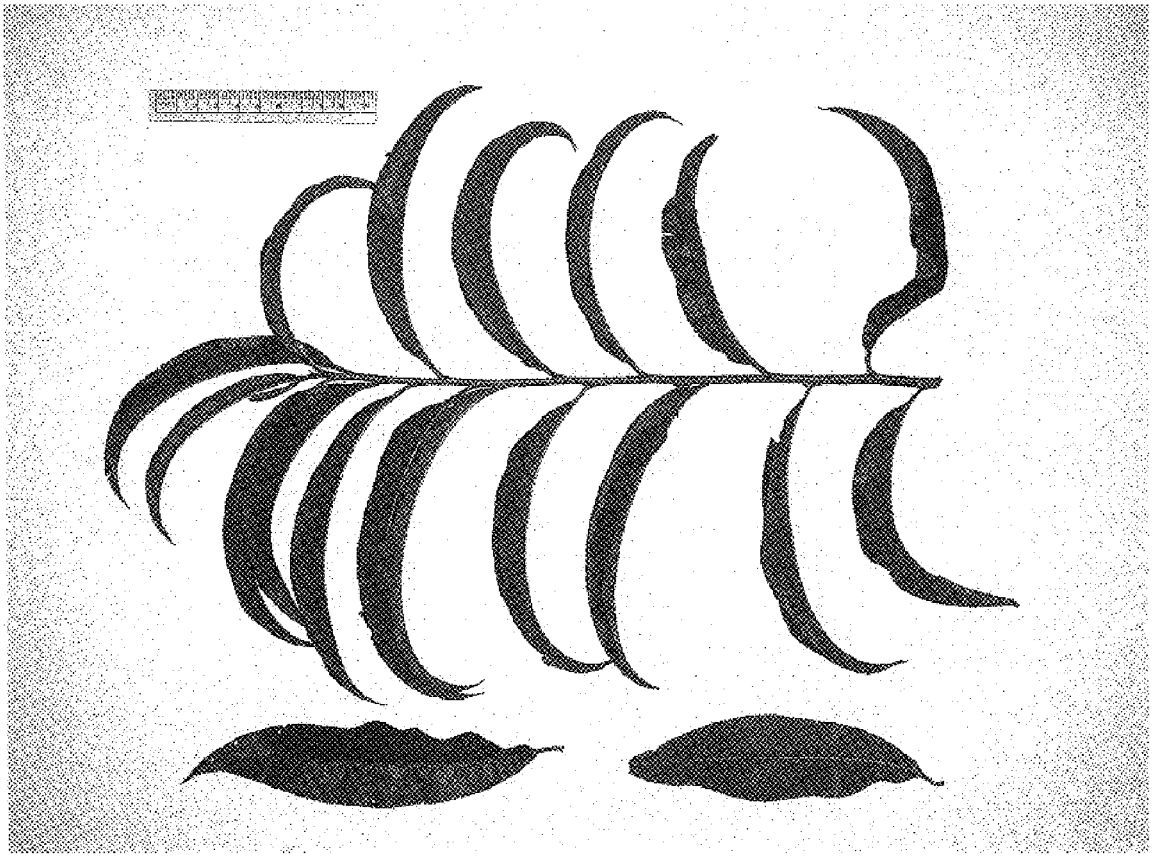
FIG. 1 is a color photograph taken on Aug. 19, 2005 of a characteristic twig of 'NJF15' in late summer bearing typical leaves of the mature foliage.
Figure 2:
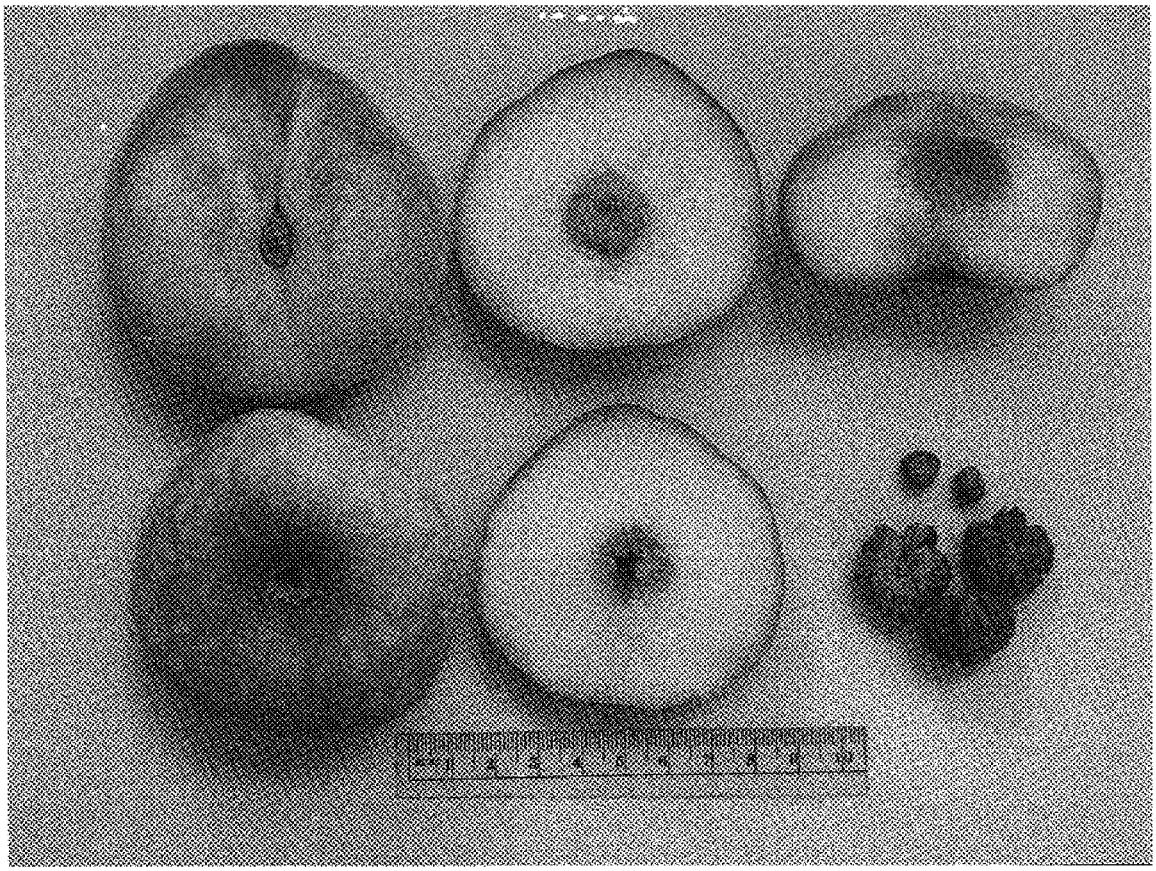
FIG. 2 is a color photograph of mature fruit of 'NJF15' and stones harvested the Rutgers Fruit Research and Extension Center in Cream Ridge, N.J. on Aug. 3, 2005. Whole fruit are presented in two positions, a basal view (upper left) and an apical view (lower left). Transverse cross sections (upper center and lower center) are presented to to show that the pericarp adheres to the pit when the fruit is mature. A longitudinal cross section (upper right) is presented to show the oblate form of the fruit. The stones (lower right) illustrate the medium height and width and deep line of the dorsal ridge and the mixture of pits and chains of pits forming grooves on the surface of the stone.
Figure 3:
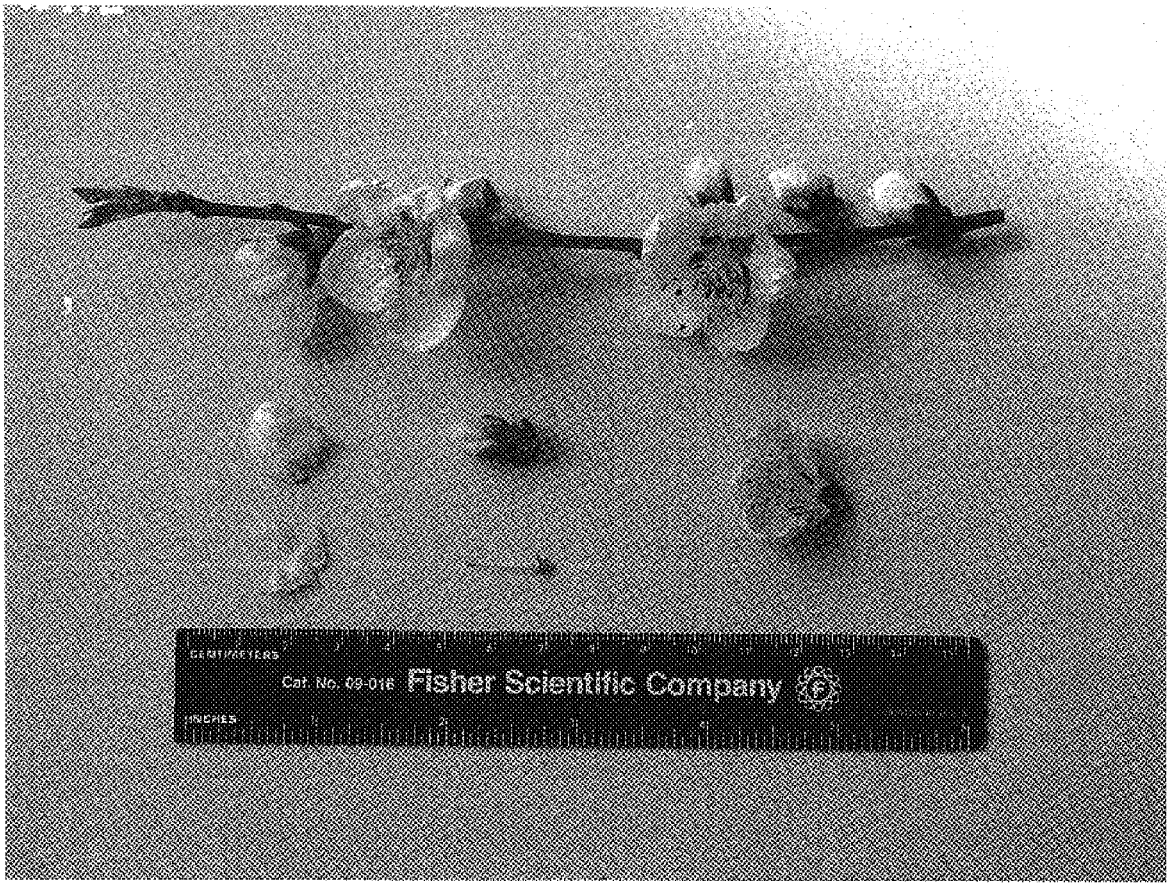
FIG. 3 is a color photograph of a characteristic twig that illustrates the typical flower buds and showy flowers of 'NJF15' observed on a tree in Cream Ridge, N.J. on Apr. 16, 2005.
Figure 4:
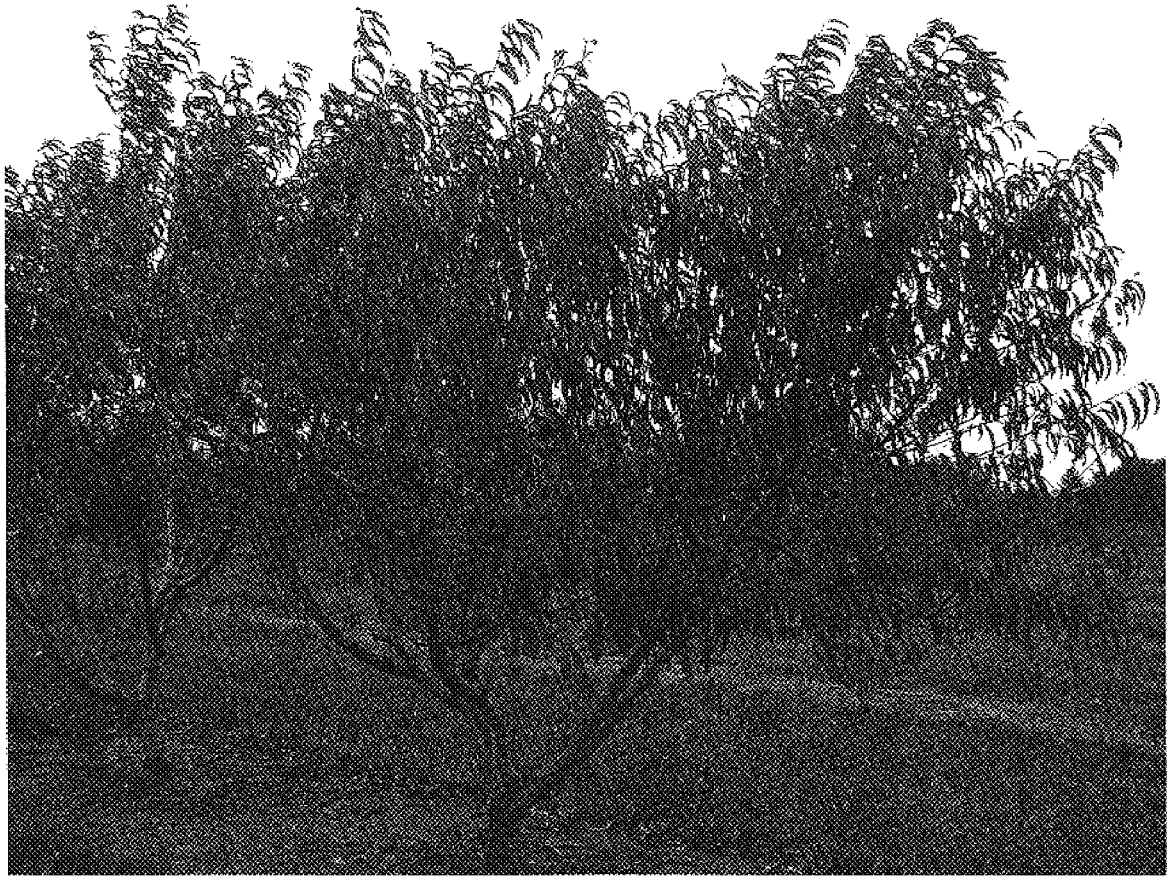
FIG. 4 is a color photograph of a tree of 'NJF15' in early fall that illustrates the moderately spreading growth habit of a tree in Cream Ridge, N.J. on Oct. 27, 2005.
Figure 5:
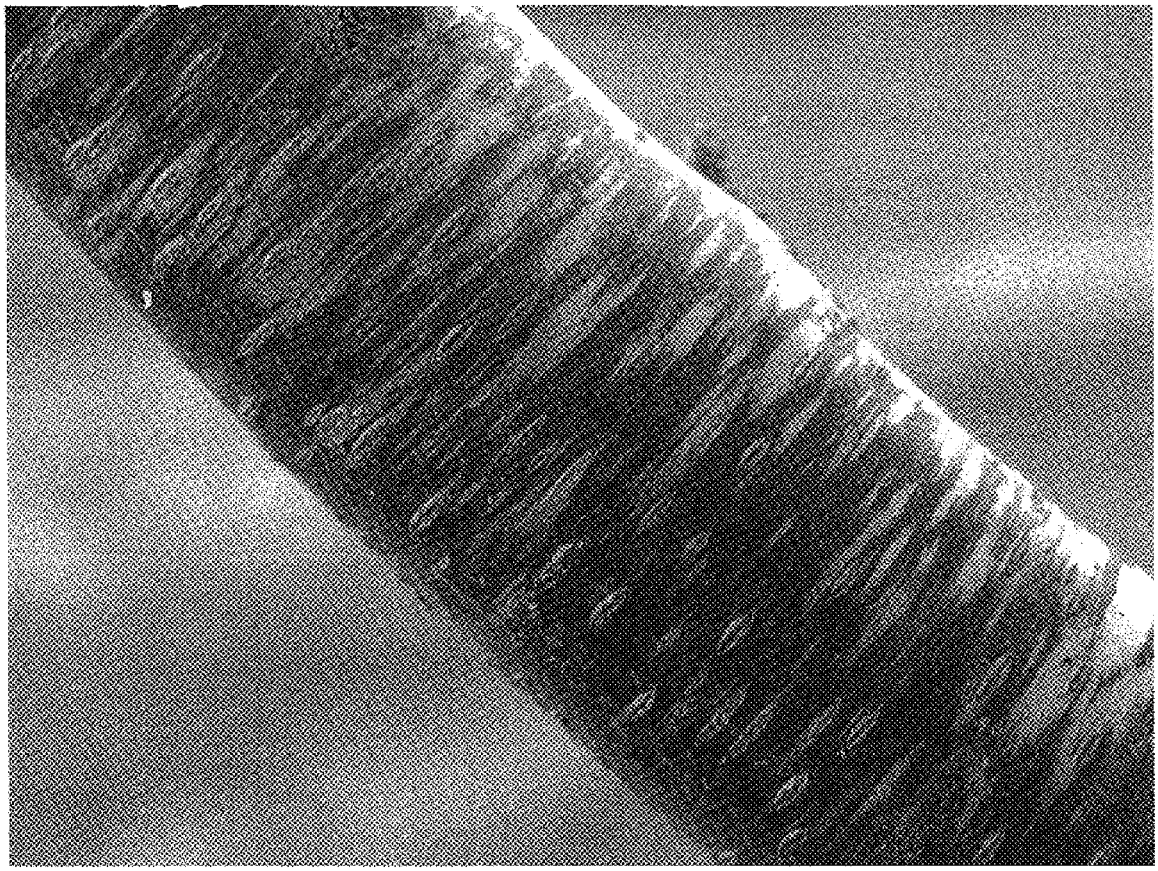
FIG. 5 is a color photograph taken on Oct. 27, 2005 of immature bark of 'NJF15' that illustrates color and the moderate density of elliptical lenticels on the immature bark.
Figure 6:
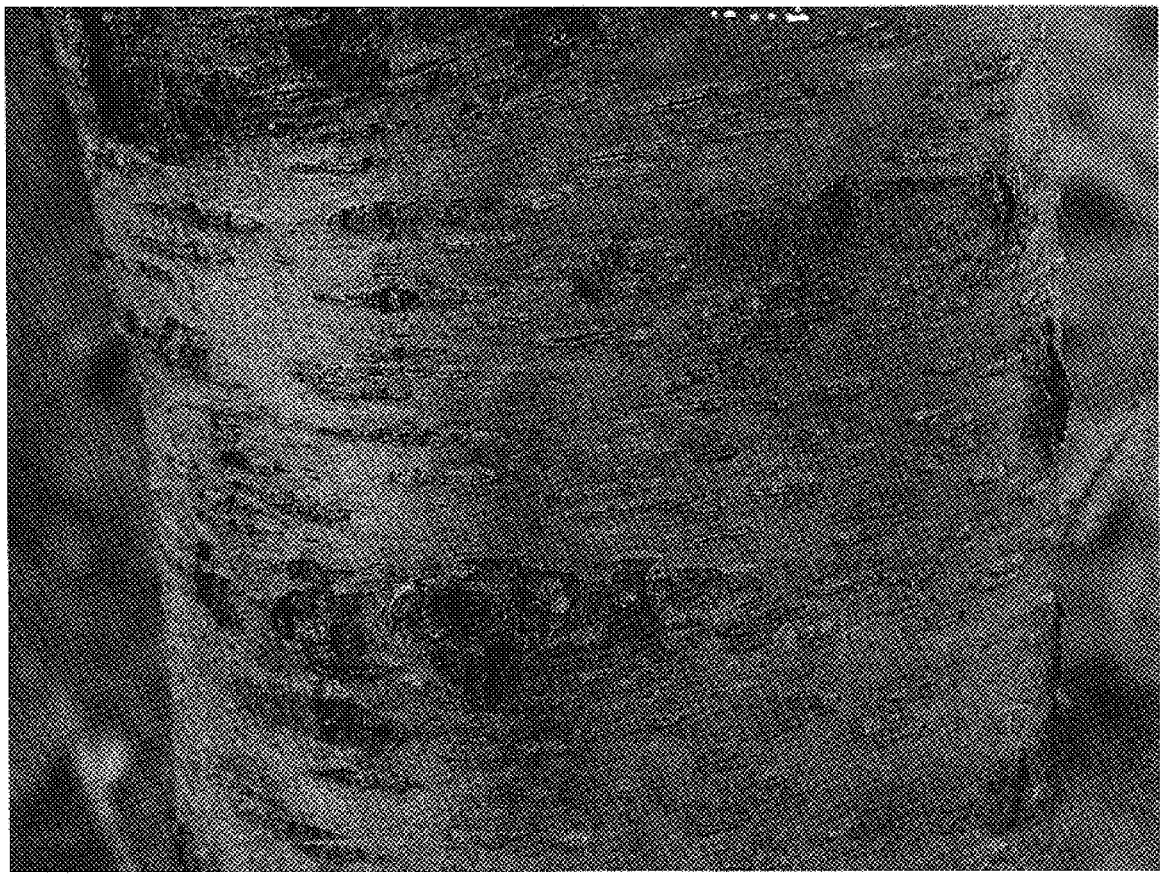
FIG. 6 is a color photograph taken on Oct. 27, 2005 of mature bark of 'NJF15' that illustrates the slightly rough texture of the mature bark.

The following detailed description of the 'NJF15' variety is based on observations of an asexually reproduced tree. The observed tree was nine years of age and growing on 'Lovell' seedling rootstock (unpatented) in Research Block C in Cream Ridge, N.J.

Latin name of genus and species: *Prunus persica* L.
Parentage:

| | |
|---|---|
| Seed parent: | B7-6-151-752080. |
| Pollen parent: | NJF7. |

Tree:

| | |
|---|---|
| Vigor: | Below average. |
| Plant hardiness zone: | Growth of plants has only been observed in zone 6b. |
| Dormant flower bud cold tolerance: | At least to −16° C. |
| Overall shape: | Slightly spreading. |
| Height: | Average as compared to other peach cultivars. For example, measurement of a typical grafted tree on 'Lovell' seedling rootstock (unpatented) at nine years after planting shows an average height of 4 meters when grown in Cream Ridge, New Jersey. |
| Width: | Below average as compared to other peach cultivars. For example, measurement of a typical grafted tree on 'Lovell' seedling rootstock (unpatented) at nine years after planting shows an average width of 4.5 meters when grown in Cream Ridge, New Jersey. |
| Caliper: | Seven year old tree is 44 cm in circumference measured at 20 cm from the ground. |

Trunk and branches:

| | |
|---|---|
| Trunk bark texture: | Slightly rough. |
| Trunk bark color: | Grey (RHS 201d). |
| Primary branches: | Branches that are approximately 15 cm in circumference are greyed-orange (RHS 176a) in color, overlaid with greyed-white (RHS 156b). |
| Lenticels: | Moderate density, approximately 2.5 per square cm; elliptical in shape; typical examples of which measured 4.5 mm in length; greyed-white (RHS 156b) in color, bordered with greyed-orange (RHS 165b). |

-continued

| | |
|---|---|
| Branch pubescence: | None. |
| New growth bark: | Color greyed-purple (RHS 183a) in sun; color yellow-green (between RHS 152a) overlaid with greyed-orange (RHS 176c) in shade. |
| Internodes: | Length 23 mm to 28 mm, averaging 26 mm on a one-year shoot. |

Leaves:

| | |
|---|---|
| Texture: | Glabrous. |
| Sheen: | Young leaves semi-glossy with a flat finish on the underside. |
| Length: | About 172 mm to 202 mm, averaging about 185 mm including the petiole. |
| Width: | About 38 mm to 48 mm, averaging about 43 mm. |
| Petiole: | About 12.9 mm long and about 1.5 mm in diameter. |
| Margin: | Serrulate. |
| Margin undulation: | Low to medium. |
| Form: | Lanceolate. |
| Apex: | Sharply acute, curved downward. |
| Base: | Broadly acute. |
| Venation: | Pinnate. |
| Glands: | |
| Number: | About 4 to 8, averaging about 5.5. |
| Position: | Located primarily on the leaf margin. |
| Size: | Length averaging 1.1 mm and width averaging 0.8 mm. |
| Form: | Reniform. |
| Stipules: | None observed on mature leaves. |
| Leaf Color: | |
| Upper leaf surface: | Yellow-green (RHS 147a to RHS 147b). |
| Lower leaf surface: | Yellow-green (RHS 148a). |
| Vein: | Yellow-green (RHS 145c). |
| Pubescence: | None. |

Flowers:

| | |
|---|---|
| Size: | Medium to large size, typical flower measuring about 38.0 mm across. |
| Color: | |
| Dormant bud: | Between grey (RHS 201b) flecked with brown (RHS 200c). |
| Pink stage bud: | Red (between RHS 56c and RHS 56d). |
| Open flower: | Red (between RHS 56c and RHS 56d). |
| Petals: | Typically five petals per flower; nearly round shape; about 19.5 mm long and 18.0 mm wide. Red (between RHS 56c and RHS 56d) in color. |
| Petal apex: | Obtuse. |
| Petal base. | Abruptly acuminate. |
| Stamens: | |
| Number: | Variable, typical range 37 to 47, averaging about 42. |
| Length: | Variable, between 13.3 mm to 17.7 mm, averaging 14.4 mm. |
| Filament color: | Green-white (RHS 157b). |
| Anther color: | Orange-red (RHS 34b). |
| Pistil: | |
| Number: | One. |
| Size: | Length between 14.7 and 15.7 mm, averaging about 15.1 mm. |
| Pistil color: | Yellow-green (RHS 145a). |
| Ovary: | Moderately pubescent, and oblate in shape. |
| Sepals: | |
| Number: | Five. |
| Pubescence: | Light. |

-continued

| | |
|---|---|
| Color: | Yellow-green (RHS 147b) with a greyed-orange (between RHS 176a to RHS 176b) over color. |
| Shape: | Triangular, with a rounded apex. |
| Size: | Length averaging 3.9 mm, width averaging 3.5 mm. |
| Nectar cup color: | Greyed-orange (RHS 167b). |
| Pollen: | Abundant; yellow-orange (between RHS 16a and 16b) in color. |
| Fragrance: | Very slight. |
| Bloom season: | Onset of bloom on Apr. 17, 2005; full bloom on Apr. 19, 2005. |

Fruit:

| | |
|---|---|
| Size: | Large for a flat peach, about 4.4 cm long, 7.0 cm wide parallel to the suture, and 7.2 cm wide perpendicular to the suture. |
| Typical weight: | 125.6 g. |
| Form: | |
| Longitudinal section: | Oblate. |
| Traverse section: | Nearly round, slightly triangular. |
| Suture: | Very shallow. |
| Ventral surface: | Slightly lipped. |
| Base: | Truncated and indented. |
| Apex: | Depressed; between 4.4 to about 7.3 mm in diameter, with an average of 5.9 mm |
| Stem: | Average length of 4.8 mm and an average diameter of 8.6 mm. |
| Skin: | |
| Thickness: | Average. |
| Surface: | Regular with short pubescence. |
| Tenacity: | Above average. |
| Astringency: | Little to none. |
| Tendency to crack: | Low. |
| Color: | Mottled red (RHS 42b) over color; ground color yellow-orange (RHS 23b). |
| Fruit Properties: | |
| Flesh color: | Yellow-orange (RHS 15a). |
| Flesh adhesion: | Clingstone. |
| Juice: | Moderate. |
| Texture: | Fine, nonmelting. |
| Fibers: | Not noticeable. |
| Ripens: | Between July 12 and July 30 at Cream Ridge, New Jersey. |
| Flavor: | Spicy. |
| Soluble solids: | 13.3%. |
| Aroma: | Strong. |

-continued

| | |
|---|---|
| Eating quality: | Very good to excellent. |
| Keeping quality: | Good: Has held its flavor and firmness for at least 21 days in cold storage at 1° C. to 4° C. |
| Shipping quality: | Good. |
| Usage: | Dessert. |
| Market: | Local and long distance. |
| Productivity: | Above average for a flat peach. Trees have produced a crop in 6 out of 7 years and a full crop in 3 out of 7 years at Cream Ridge, New Jersey. |

Stone:

| | |
|---|---|
| Type: | Clingstone. |
| Form: | Oblate. |
| Base: | Very broad. |
| Apex: | Very broad. |
| Surface: | Mixture of pits and chains of pits forming grooves. |
| Ventral suture: | High and deeply grooved on both sides. |
| Dorsal ridge: | Medium height and width, and deep lines. |
| External Color: | Greyed-orange (between RHS 165b and RHS 165d). |
| Internal color when cracked: | Greyed-orange (RHS 165d). |
| Cavity surface color: | Greyed-orange (RHS 165d). |
| Average stone weight: | Dry weight 2.9 g. |
| Average stone wall thickness: | Variable, between 3.1 and 6.7 mm. |
| Size: | Averages about 16.0 mm long, 23.0 mm wide parallel to the dorsal ridge, and 22.0 mm wide perpendicular to the dorsal ridge. |
| Tendency to split: | None. |
| Kernel: | |
| Form: | Irregular. |
| Skin color: | Greyed-orange (RHS 163c). |
| Vein color: | Greyed-orange (RHS 165b). |
| Viable: | No. |
| Size: | Highly variable; forms only rudimentary seed. |
| Amygdalin | Present |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *